(12) United States Patent
Ikeda

(10) Patent No.: US 12,562,265 B2
(45) Date of Patent: Feb. 24, 2026

(54) ENDOSCOPE CLEANING MANAGEMENT SYSTEM, ENDOSCOPE CLEANING MANAGEMENT METHOD, AND RECORDING MEDIUM

(71) Applicant: OLYMPUS CORPORATION, Tokyo (JP)

(72) Inventor: Yoshiko Ikeda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 657 days.

(21) Appl. No.: 17/847,321

(22) Filed: Jun. 23, 2022

(65) Prior Publication Data

US 2022/0336091 A1 Oct. 20, 2022

Related U.S. Application Data

(63) Continuation of application No. PCT/JP2019/051298, filed on Dec. 26, 2019.

(51) Int. Cl.
*G16H 40/40* (2018.01)
*A61B 1/00* (2006.01)
*A61B 1/12* (2006.01)

(52) U.S. Cl.
CPC ......... *G16H 40/40* (2018.01); *A61B 1/00055* (2013.01); *A61B 1/126* (2013.01); *A61L 2202/24* (2013.01)

(58) Field of Classification Search
CPC .... G16H 40/40; A61B 1/00055; A61B 1/126; A61L 2202/24
See application file for complete search history.

(56) References Cited

U.S. PATENT DOCUMENTS

| 2015/0278460 | A1* | 10/2015 | Miura | ................ | A61B 1/00059 |
| | | | | | 705/2 |
| 2018/0102189 | A1* | 4/2018 | Hosoi | .................... | G16H 40/20 |

FOREIGN PATENT DOCUMENTS

| JP | 2009-136415 A | 6/2009 |
| JP | 2009-268508 A | 11/2009 |

(Continued)

OTHER PUBLICATIONS

International Preliminary Report on Patentability dated Jun. 28, 2022 and Written Opinion dated Feb. 18, 2020 received in PCT/JP2019/051298.

(Continued)

*Primary Examiner* — Amy Ng
*Assistant Examiner* — Anthony G Gemignani
(74) *Attorney, Agent, or Firm* — Scully, Scott, Murphy & Presser, P.C.

(57) ABSTRACT

A cleaning apparatus management unit manages the utilization status of a first cleaning apparatus that can clean an endoscope that has been manually cleaned in a procedure in which one or more steps are skipped and the utilization status of a second cleaning apparatus that can clean an endoscope that has been manually cleaned by performing all the steps. A reception unit receives step information indicating a completed step during the manual cleaning of the endoscope. When the received step information indicates a predetermined step that comes before a final step, an assignment processing unit determines a cleaning apparatus to be assigned to the endoscope based on the relationship between scheduled completion time of the manual cleaning when the implementation of the one or more steps that come after the predetermined step is skipped and the utilization status of a plurality of cleaning apparatuses managed by the cleaning apparatus management unit.

9 Claims, 7 Drawing Sheets

| SCOPE MODEL | STEP NUMBER | WHETHER OR NOT STEP CAN BE SKIPPED | MODEL OF CLEANING APPARATUS AVAILABLE WHEN STEP IS SKIPPED |
|---|---|---|---|
| AAA | 1 | ✕ (CANNOT BE SKIPPED) | ---- |
| | 2 | ✕ (CANNOT BE SKIPPED) | ---- |
| | 3 | ◯ (CAN BE SKIPPED) | XXX,YYY,ZZZ |
| | 4 | ◯ (CAN BE SKIPPED) | XXX,YYY,ZZZ |
| | 5 | ◯ (CAN BE SKIPPED) | XXX,YYY,ZZZ |
| | 6 | ◯ (CAN BE SKIPPED) | XXX,YYY,ZZZ |
| | 7 | ◯ (CAN BE SKIPPED) | XXX,YYY,ZZZ |
| | 8 | ✕ (CANNOT BE SKIPPED) | ---- |

(56)                    References Cited

FOREIGN PATENT DOCUMENTS

| JP | 2017-117295 | A | 6/2017 |
| JP | 2017-131335 | A | 8/2017 |
| WO | 2019/049439 | A1 | 3/2019 |

OTHER PUBLICATIONS

International Search Report dated Feb. 18, 2020 received in PCT/JP2019/051298.

* cited by examiner

FIG.3

| SCOPE MODEL | STEP NUMBER | WORK DETAILS OF STEP | FILE |
|---|---|---|---|
| AAA | 1 | BRUSHING OF FORCEPS RAISING BASE | VIDEO IMAGE 1 |
| | 2 | BRUSHING OF CHANNELS | VIDEO IMAGE 2 |
| | 3 | SUCTION OF CLEANING SOLUTION THROUGH FORCEPS AND SUCTION CHANNELS | VIDEO IMAGE 3 |
| | 4 | DELIVERY OF CLEANING SOLUTION TO AIR SUPPLY AND WATER SUPPLY CHANNELS | VIDEO IMAGE 4 |
| | 5 | DELIVERY OF CLEANING SOLUTION TO SECONDARY WATER SUPPLY CHANNEL | VIDEO IMAGE 5 |
| | 6 | IMMERSION IN DISINFECTANT | VIDEO IMAGE 6 |
| | 7 | REMOVAL OF CLEANING SOLUTION FROM ALL CHANNELS | VIDEO IMAGE 7 |
| | 8 | DRYING OF OUTER SURFACE | VIDEO IMAGE 8 |

| SCOPE ID | STEP NUMBER | IMPLEMENTATION RECORD |
|---|---|---|
| 105011 | 1 | |
| | 2 | |
| | 3 | |
| | 4 | |
| | 5 | |
| | 6 | |
| | 7 | |
| | 8 | |

| SCOPE MODEL | STEP NUMBER | WHETHER OR NOT STEP CAN BE SKIPPED | MODEL OF CLEANING APPARATUS AVAILABLE WHEN STEP IS SKIPPED |
|---|---|---|---|
| AAA | 1 | × (CANNOT BE SKIPPED) | — |
| | 2 | × (CANNOT BE SKIPPED) | — |
| | 3 | ○ (CAN BE SKIPPED) | XXX,YYY,ZZZ |
| | 4 | ○ (CAN BE SKIPPED) | XXX,YYY,ZZZ |
| | 5 | ○ (CAN BE SKIPPED) | XXX,YYY,ZZZ |
| | 6 | ○ (CAN BE SKIPPED) | XXX,YYY,ZZZ |
| | 7 | ○ (CAN BE SKIPPED) | XXX,YYY,ZZZ |
| | 8 | × (CANNOT BE SKIPPED) | — |

| SCOPE ID | STEP NUMBER | IMPLEMENTATION RECORD |
|---|---|---|
| 105011 | 1 | 9:56:15 |
| | 2 | 10:00:00 |
| | 3 | |
| | 4 | |
| | 5 | |
| | 6 | |
| | 7 | |
| | 8 | |

| APPARATUS NUMBER | CLEANING APPARATUS (NAME) | CLEANING APPARATUS MODEL | CLEANING APPARATUS ID | STATUS | REMAINING CLEANING TIME |
|---|---|---|---|---|---|
| 1 | FIRST CLEANING APPARATUS 12a | XXX | 345678 | AVAILABLE | — |
| 2 | FIRST CLEANING APPARATUS 12b | XXX | 345679 | IN USE | 2:15 |
| 3 | FIRST CLEANING APPARATUS 12c | YYY | 534621 | IN USE | 7:28 |
| 4 | FIRST CLEANING APPARATUS 12d | XXX | 346000 | IN USE | 12:07 |
| 5 | SECOND CLEANING APPARATUS 12e | mmm | 892312 | AVAILABLE | UNKNOWN |
| 6 | SECOND CLEANING APPARATUS 12f | nnn | 792357 | IN USE | UNKNOWN |

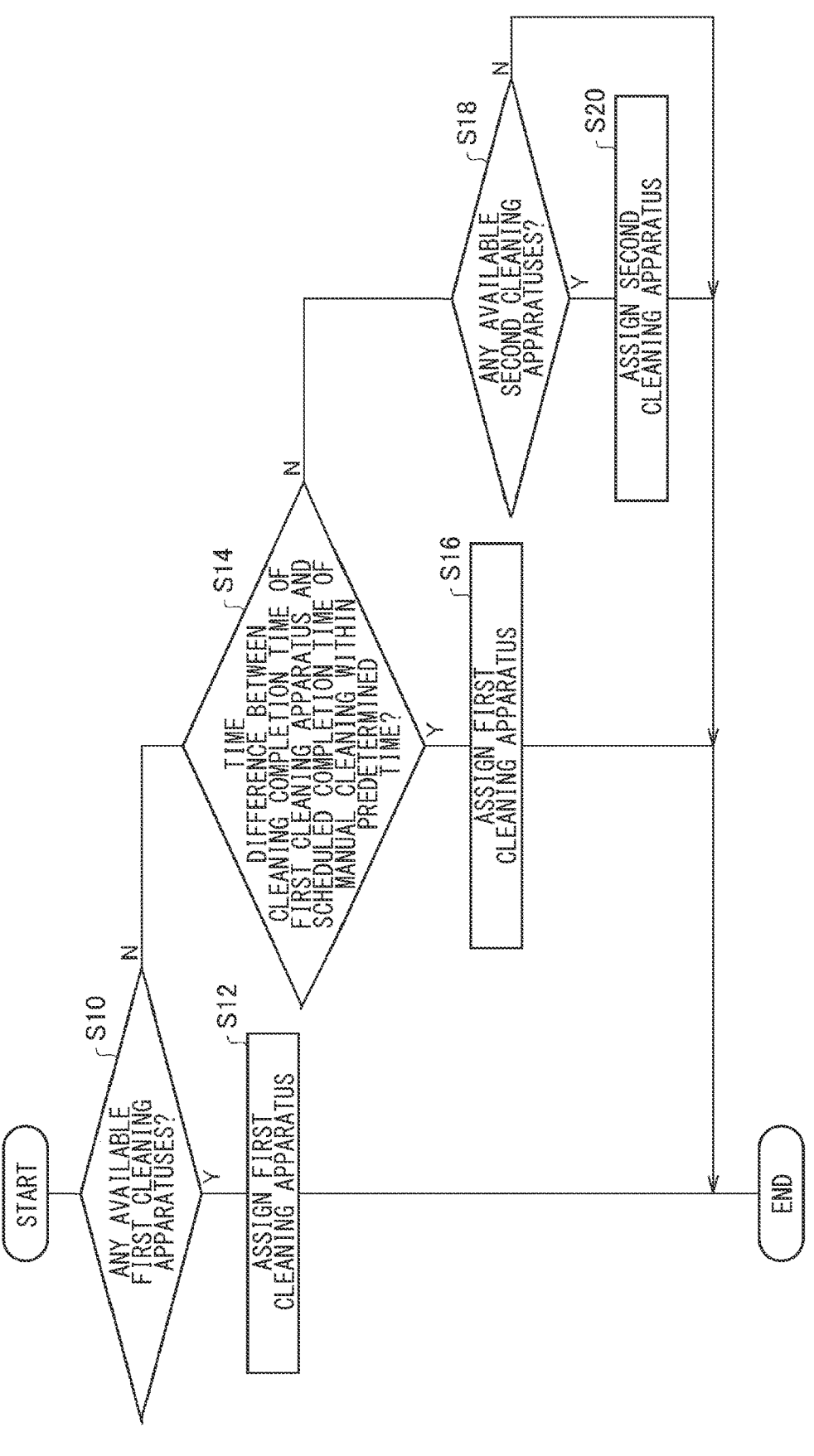

START

S10 ANY AVAILABLE FIRST CLEANING APPARATUSES?

S12 ASSIGN FIRST CLEANING APPARATUS

S14 TIME DIFFERENCE BETWEEN CLEANING COMPLETION TIME OF FIRST CLEANING APPARATUS AND SCHEDULED COMPLETION TIME OF MANUAL CLEANING WITHIN PREDETERMINED TIME?

S16 ASSIGN FIRST CLEANING APPARATUS

S18 ANY AVAILABLE SECOND CLEANING APPARATUSES?

S20 ASSIGN SECOND CLEANING APPARATUS

END

FIG.9

| SCOPE ID | STEP NUMBER | IMPLEMENTATION RECORD |
|----------|-------------|----------------------|
| 105011 | 1 | 9:56:15 |
| | 2 | 10:00:00 |
| | 3 | (SKIP) |
| | 4 | (SKIP) |
| | 5 | (SKIP) |
| | 6 | (SKIP) |
| | 7 | (SKIP) |
| | 8 | 10:03:05 |

96

ENDOSCOPE CLEANING MANAGEMENT SYSTEM, ENDOSCOPE CLEANING MANAGEMENT METHOD, AND RECORDING MEDIUM

BACKGROUND

1. Field of the Disclosure

The present disclosure relates to technology for managing the implementation of manual cleaning of endoscopes.

2. Description of the Related Art

In Japan, the Japan Gastroenterological Endoscopy Society published "Guidelines for Cleaning and Disinfecting Gastroenterological Endoscopy Equipment" in 1998, and in medical facilities, cleaning and disinfection are carried out in accordance with the published guidelines to prevent infection caused by endoscopic examination. In order to efficiently perform cleaning and disinfection of endoscopes, endoscope cleaning apparatuses that automatically perform a cleaning process, a disinfection process, and a rinsing process are used in many medical facilities.

High-action disinfectants are used in endoscope cleaning apparatuses. However, protein residues such as mucus and blood of patients reduce the effectiveness of high-action disinfectants. Therefore, before setting an endoscope in a cleaning tank of an endoscope cleaning apparatus, the cleaning worker needs to remove protein residues by manual cleaning.

Patent Literature 1 discloses an endoscope cleaning management system that evaluates the skill level of a cleaning worker in a manual cleaning operation. In this system, during manual cleaning by a cleaning worker, work procedure information including detailed implementation items in each step of the work is displayed on a display apparatus.

[Patent Literature 1] Japanese Patent Application Publication NO. 2017-131335

Since endoscopes have different structures for each model, endoscope manufacturers define a manual cleaning procedure consisting of multiple steps for each model. A cleaning worker manually cleans an endoscope used for an examination according to the procedure for the model and then sets the manually cleaned endoscope in a cleaning apparatus for machine cleaning.

Cleaning apparatuses that can clean manually-cleaned endoscopes in a procedure in which one or more steps are skipped are currently available. One of the purposes of manual cleaning is to remove a protein residue, and if a cleaning apparatus has a function of removing a protein residue from an endoscope, the corresponding step in manual cleaning can be skipped.

To be able to reduce the time required for manual cleaning is a major advantage for medical facilities. Therefore, it is ideal that all cleaning apparatuses in medical facilities are provided with a function of removing a protein residue so that steps of the manual cleaning can be skipped. However, in reality, cleaning apparatuses having a function of removing a protein residue and cleaning apparatuses not having such a function are mixedly present. In such an environment where multiple types of cleaning apparatuses are mixedly present, there is a need for a technology for efficiently managing a manual cleaning by cleaning workers.

SUMMARY

In this background, a purpose of the present disclosure is to provide a technology for managing manual cleaning properly by cleaning workers.

One embodiment of the present disclosure relates to an endoscope cleaning management system for managing implementation of a manual cleaning of an endoscope consisting of a plurality of steps, including: a cleaning apparatus management unit that manages the utilization status of a first cleaning apparatus that can clean an endoscope that has been manually cleaned in a procedure in which one or more steps are skipped and the utilization status of a second cleaning apparatus that cannot clean an endoscope that has been manually cleaned in a procedure in which one or more steps are skipped but can clean an endoscope that has been manually cleaned by performing all the steps; a first identification information acquisition unit that acquires identification information for identifying an endoscope to be manually cleaned; a reception unit that receives step information indicating a completed step during the manual cleaning of the endoscope; and an assignment processing unit that determines, when the received step information indicates a predetermined step that comes before a final step, a cleaning apparatus to be assigned to the endoscope based on the relationship between scheduled completion time of the manual cleaning when the implementation of the one or more steps that come after the predetermined step is skipped and the utilization status of a plurality of cleaning apparatuses managed by the cleaning apparatus management unit.

Optional combinations of the aforementioned constituting elements and implementations of the disclosure in the form of methods, apparatuses, systems, recording mediums, and computer programs may also be practiced as additional modes of the present disclosure.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which:

FIG. 3 is a diagram showing an example of work details of each step of manual cleaning;

FIG. 4 is a diagram showing examples of recording details in an implementation recording unit;

FIG. 5 is a diagram showing an example of a step skipping condition;

FIG. 6 is a diagram showing examples of recording details in the implementation recording unit;

FIG. 7 is a diagram showing a management table for managing the utilization status of a plurality of cleaning apparatuses;

FIG. 8 is a flowchart showing a determination process of a cleaning apparatus; and FIG. 9 is a diagram showing examples of recording details in the implementation recording unit.

DETAILED DESCRIPTION

The disclosure will now be described by reference to the preferred embodiments. This does not intend to limit the scope of the present disclosure, but to exemplify the disclosure.

Figure 1:
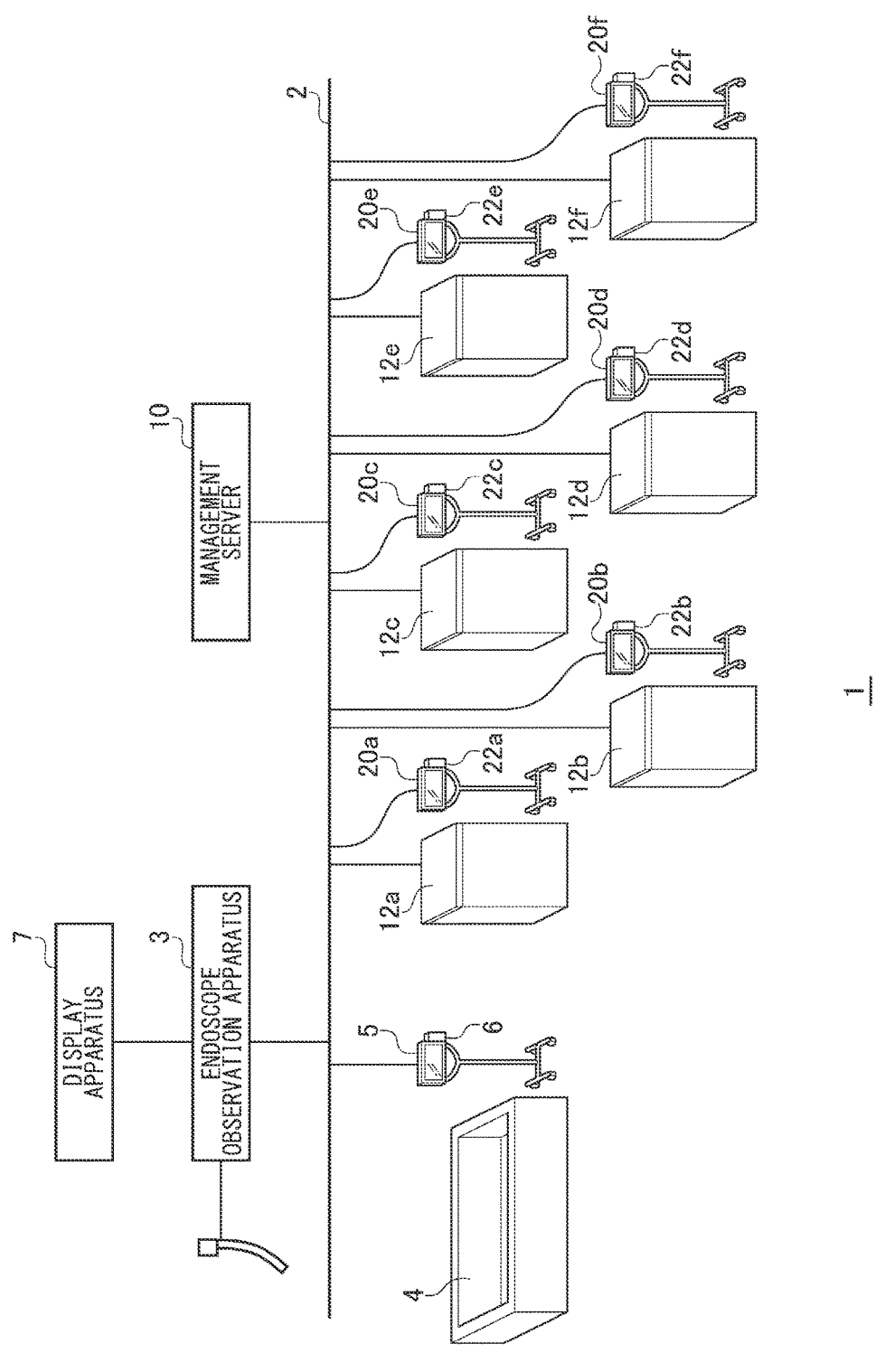
FIG. 1 is a diagram showing the configuration of a cleaning management system according to an embodiment.

FIG. 1 shows the configuration of a cleaning management system 1 according to an embodiment of the present disclosure. The cleaning management system 1 is a system for managing the cleaning process of an endoscope used in an examination and includes an endoscope observation apparatus 3 and a management server 10.

The endoscope observation apparatus 3 is placed in an examination room. When an endoscope is connected to the endoscope observation apparatus 3 before the start of an examination, the endoscope observation apparatus 3 acquires identification information (scope ID) of the endoscope and transmits the scope ID and information related to the examination to the management server 10. When the examination is started, the endoscope observation apparatus 3 processes image data acquired by the endoscope and displays a captured image on a display apparatus 7. Further, the endoscope observation apparatus 3 acquires the captured image at the time when a release switch of the endoscope is pressed and transmits the captured image to an image server (not shown).

In a cleaning room of a medical facility, a sink 4 for manual cleaning of endoscopes and a plurality of cleaning apparatuses 12a to 12f for mechanical cleaning of manually cleaned endoscopes are provided. In the embodiment, four first cleaning apparatuses 12a, 12b, 12c and 12d and two second cleaning apparatuses 12e and 12f are provided. The first cleaning apparatuses 12a to 12d have a function of removing a protein residue from endoscopes used in examinations, while the second cleaning apparatuses 12e and 12f do not have the function of removing a protein residue. Hereinafter, the first cleaning apparatuses 12a to 12d and the second cleaning apparatuses 12e to 12f may be referred to as "cleaning apparatuses 12" when no particular distinction is to be made. The cleaning room may be provided with a plurality of sinks 4.

Each cleaning apparatus 12 is provided with a terminal apparatus 20 such as a tablet and an ID reader 22 for reading the identification information (scope ID) of an endoscope to be mechanically cleaned in association with the cleaning apparatus. More specifically, a terminal apparatus 20a and an ID reader 22a are associated with the first cleaning apparatus 12a, the ID reader 22a reads the scope ID of an endoscope to be mechanically cleaned in the first cleaning apparatus 12a before the start of the cleaning, and the terminal apparatus 20a displays information related to the endoscope from which the scope ID has been read and information related to the first cleaning apparatus 12a on a display. As shown in the figure, a terminal apparatus 20b and an ID reader 22b are associated with the first cleaning apparatus 12b, a terminal apparatus 20c and an ID reader 22c are associated with the first cleaning apparatus 12c, a terminal apparatus 20d and an ID reader 22d are associated with the first cleaning apparatus 12d, a terminal apparatus 20e and an ID reader 22e are associated with the second cleaning apparatus 12e, and a terminal apparatus 20f and an ID reader 22f are associated with the second cleaning apparatus 12f. On the side of a sink 4, a terminal apparatus 5 such as a tablet and an ID reader 6 for reading the scope ID of an endoscope to be manually cleaned are provided in association with the sink 4.

In a medical facility, a tape printed with a scope ID is attached to an endoscope, and a cleaning worker causes the ID reader 6 or the ID reader 22 to read the scope ID before the start of the manual cleaning or the mechanical cleaning. The ID reader 6 or the ID reader 22 transmits the read scope ID to the management server 10, and the management server 10 thereby manages the cleaning status of the endoscope. The scope ID may be recorded in an RFID tag and may be read in a contactless manner by the ID reader 6 or the ID reader 22, which are RFID readers.

After the examination is completed, the cleaning worker wipes the outer surface of the endoscope and performs a suction cleaning of suction and forceps channels in the examination room. The cleaning process is also called bedside cleaning, and the cleaning worker places the cleaned endoscope in a dedicated container and carries the dedicated container to the cleaning room.

In the cleaning room, the cleaning worker causes the ID reader 6 to read the scope ID, and the ID reader 6 transmits the read scope ID to the management server 10. Upon acquiring the scope ID from the ID reader 6, the management server 10 provides the terminal apparatus 5 with an image that guides the work details of a manual cleaning for a model corresponding to the scope ID.

The manual cleaning of an endoscope needs to be performed in accordance with a procedure consisting of multiple steps defined according to each endoscope model. Therefore, guidance images are provided in the form of animations or illustrations that guide the work details of the manual cleaning and that are easy for the cleaning worker to understand the work details to be performed.

The terminal apparatus 5 displays a guidance image for each step, and the cleaning worker performs each step of the cleaning procedure while checking a guidance image displayed on the terminal apparatus 5. Upon completing one step of the cleaning procedure, the cleaning worker enters the completion of the step in the terminal apparatus 5. If the terminal apparatus 5 has a touch panel, the cleaning worker may enter the completion of the step by taking off his/her gloves and touching a step ending button displayed on the display. A foot pedal connected to the terminal apparatus 5 may be provided at the foot of the cleaning worker, and the cleaning worker may enter the completion of the step by stepping on the foot pedal. The completion of the step may also be entered into the terminal apparatus 5 through the speaking of a predetermined phrase by the cleaning worker followed by the reception of the spoken sound by the microphone of the terminal apparatus 5. The predetermined phrase may be, for example, "I have completed this step". Upon receiving an entry indicating the completion of the step, the terminal apparatus 5 transmits step information indicating the completed step to the management server 10.

Upon receiving the step information indicating the completed step from the terminal apparatus 5, the management server 10 provides the terminal apparatus 5 with a guidance image of the work details of the next step. In this way, the management server 10 supports the manual cleaning work performed by the cleaning worker.

In the cleaning management system 1 according to the embodiment, the first cleaning apparatuses 12a to 12d belong to models that have a function of removing a protein residue from endoscopes and that can clean endoscopes that have been manually cleaned in a procedure in which the implementation of one or more steps is skipped. The first cleaning apparatuses 12a to 12d are capable of removing a protein residue only from several models of endoscopes that exist in medical facilities. In other words, endoscopes from which a protein residue can be removed may be limited to those of certain models. For example, the first cleaning apparatuses 12a to 12d have a function of removing a protein residue from endoscopes manufactured by the same manufacturer.

On the other hand, the second cleaning apparatuses 12e to 12f belong to models that do not have a function of removing a protein residue from endoscopes and that cannot clean endoscopes that have been manually cleaned in a procedure in which the implementation of one or more steps is skipped.

In other words, endoscopes that can be cleaned by the second cleaning apparatuses 12*e* to 12*f* are limited to endoscopes that have been manually cleaned by performing all the steps. Therefore, when using the cleaning apparatuses 12*e* to 12*f*, the endoscopes need to have been manually cleaned by performing all the steps. If one or more steps are skipped, the endoscopes need to be manually cleaned again.

Figure 2:
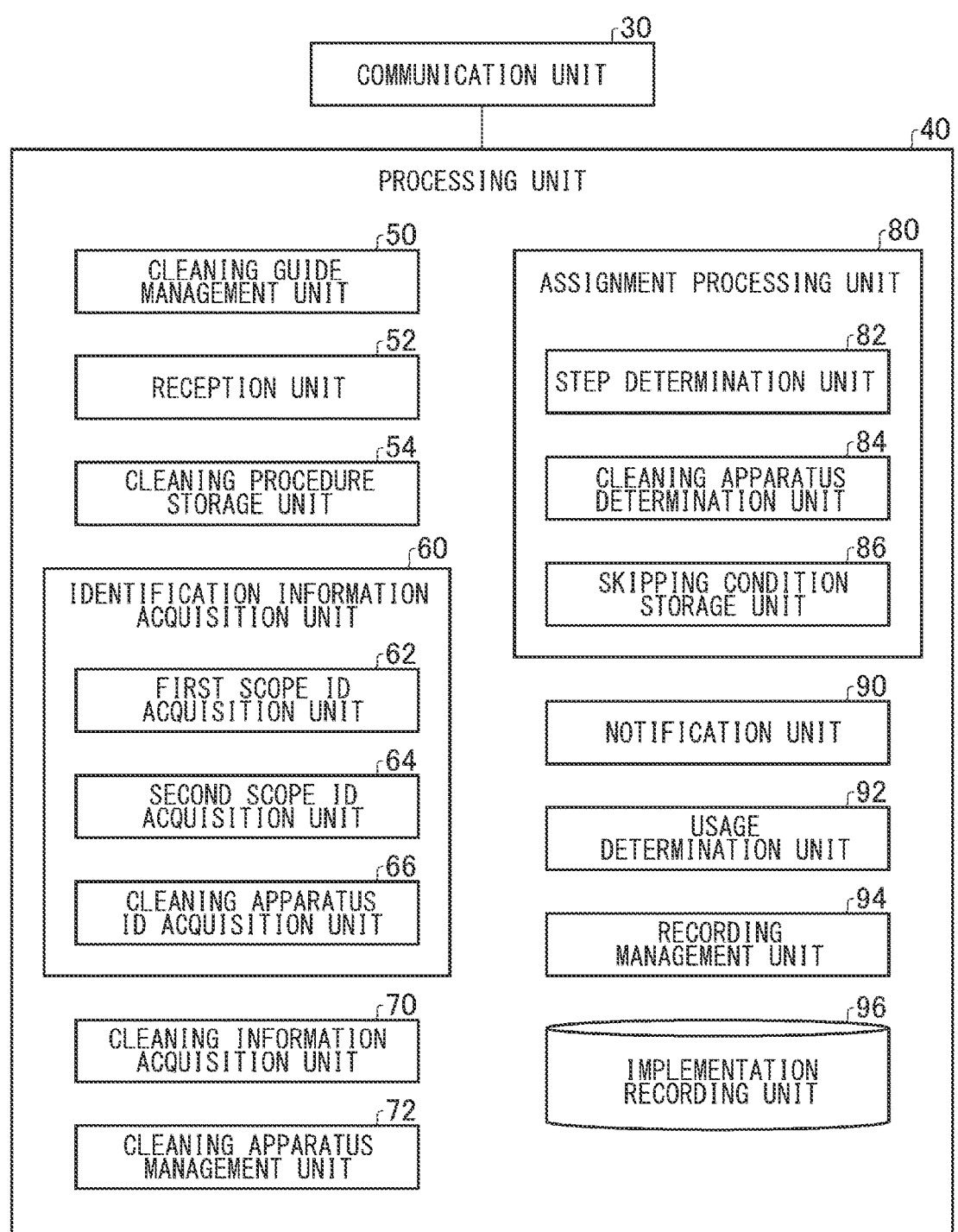
FIG. 2 is a diagram showing functional blocks of a management server.

FIG. 2 shows functional blocks of the management server 10. The management server 10 includes a communication unit 30 and a processing unit 40. The communication unit 30 is connected to the endoscope observation apparatus 3, the terminal apparatus 5, the ID reader 6, the cleaning apparatus 12, the terminal apparatus 20, and the ID reader 22 by a network 2 such as a local area network (LAN).

The processing unit 40 includes a cleaning guide management unit 50, a reception unit 52, a cleaning procedure storage unit 54, an identification information acquisition unit 60, a cleaning information acquisition unit 70, a cleaning apparatus management unit 72, an assignment processing unit 80, a notification unit 90, a usage determination unit 92, a recording management unit 94, and an implementation recording unit 96. The identification information acquisition unit 60 has a first scope ID acquisition unit 62, a second scope ID acquisition unit 64, and a cleaning apparatus ID acquisition unit 66, and the assignment processing unit 80 has a step determination unit 82, a cleaning apparatus determination unit 84, and a skipping condition storage unit 86.

The configuration thereof is implemented by hardware such as an arbitrary processor, a memory, auxiliary storage, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

The cleaning procedure storage unit 54 stores guidance images showing the work details of multiple steps of a manual cleaning for each endoscope model. FIG. 3 shows an example of the work details of each step of a manual cleaning stored in the cleaning procedure storage unit 54. The manual cleaning procedure consists of multiple steps. In relation to a model ID that identifies the scope model, the cleaning procedure storage unit 54 stores a step number and a video image showing the work details of the step in association with each other. The cleaning worker performs each step in accordance with the order of the step number. FIG. 3 shows the work details of cleaning steps for a scope model AAA. The cleaning procedure storage unit 54 stores the details of cleaning steps for all the models of endoscope possessed by the medical facility in association with model IDs.

Before the start of the manual cleaning, the cleaning worker causes the ID reader 6 to read the scope ID of an endoscope to be manually cleaned next. It is assumed that the read scope ID is "105011". The ID reader 6 transmits the read scope ID to the management server 10 along with the identification information (reader ID) of the ID reader 6.

In the management server 10, the communication unit 30 receives the scope ID and the reader ID transmitted from the ID reader 6, and the first scope ID acquisition unit 62 acquires the scope ID and the reader ID. The scope ID "105011" is identification information that identifies the endoscope to be manually cleaned next, and the recording management unit 94 records the acquired scope ID in the implementation recording unit 96. The scope IDs of the endoscopes possessed by the medical facility are recorded in an endoscope master table (not shown) along with attribute information such as scope model, manufacturer, date and time of purchase, and start date of use. The recording management unit 94 identifies the scope model from the master table based on the scope ID, acquires the number of steps for a manual cleaning associated with the scope model by referring to the cleaning procedure storage unit 54, and generates a record that records implementation information. In this case, based on the master table, the scope model with the scope ID "105011" is identified as "AAA", and the number of steps for the manual cleaning is acquired as eight.

FIG. 4 shows examples of recording details in the implementation recording unit 96. The recording management unit 94 generates a record in which implementation information indicating that a step has been implemented is written for step numbers 1 to 8. In the embodiment, the implementation information to be written is time information for when a step has been completed, and the recording management unit 94 records the time information for when the step has been completed, based on the step information received by the reception unit 52, in the implementation recording unit 96 in connection with the scope ID.

Upon acquisition of the scope ID by the first scope ID acquisition unit 62, the cleaning guide management unit 50 reads a video image file stored for the scope model AAA from the cleaning procedure storage unit 54 and supplies the video image file to the terminal apparatus 5. The cleaning guide management unit 50 reads a video image file in the order of the step number. Thus, the cleaning guide management unit 50 first reads a video image 1 and supplies the video image 1 to the terminal apparatus 5. The terminal apparatus 5 reproduces and displays the video image 1 on the display.

Although the cleaning procedure storage unit 54 is provided in the management server 10 in the embodiment, the cleaning procedure storage unit 54 may be provided in the terminal apparatus 5 in another embodiment. In this case, the cleaning guide management unit 50 may notify the terminal apparatus 5 of a scope model name and a step number to be reproduced, and the terminal apparatus 5 may read a video image file corresponding to the scope model name and the step number and reproduce and display the video image file on the display. The video image file may also be recorded in another image server, and terminal apparatus 5 may be provided with the video image file from the image server.

The video image 1 that is reproduced and displayed on the terminal apparatus 5 is a video image that shows the work details of the step 1 in the endoscope cleaning procedure and shows the way to brush a forceps raising base. For example, the video image may be a skilled person's model video image. The cleaning worker looks at the video image 1 displayed on the terminal apparatus 5, checks the correct way of performing the brushing, and brushes the forceps raising base. When the brushing of the forceps raising base is completed, the cleaning worker enters the completion of the step 1 in the terminal apparatus 5. As described above, the entry of the completion of the step may be performed by touch panel operation, foot pedal operation, or voice input. At this time, the terminal apparatus 5 transmits step information indicating the completion of the step 1 to management server 10 along with the scope ID.

At the management server 10, the reception unit 52 receives the scope ID and the step information indicating the completed step. In this example, the reception unit 52 receives the step information indicating that the step 1 has been completed and supplies the step information and the scope ID to the assignment processing unit 80. The reception unit 52 also notifies the recording management unit 94 of the step information, the date and time of the acquisition of the step information, and the scope ID, and the recording management unit 94 records the completion time of the step 1 in the implementation recording unit 96 in connection with the scope ID "105011".

In the assignment processing unit 80, the skipping condition storage unit 86 stores a condition for skipping the implementation of one or more steps of the manual cleaning for each scope model. FIG. 5 shows an example of a step skipping condition stored in the skipping condition storage unit 86. FIG. 5 shows a step skipping condition for the scope model AAA. The skipping condition storage unit 86 stores the step skipping conditions for all the models of the endoscopes possessed by the medical facility.

The skipping condition storage unit 86 stores a step skipping condition in which step numbers that can be skipped are associated with model information of cleaning apparatuses that can be used when the steps are skipped. As a step skipping condition, FIG. 5 shows, with regard to the endoscope of the scope model AAA, that the use of a cleaning apparatus 12 of a model XXX, YYY, or ZZZ allows for the skipping of five steps from a step number 3 to a step number 7 of the manual cleaning.

When the reception unit 52 receives step information from the terminal apparatus 5, the step determination unit 82 determines whether or not the received step information indicates a predetermined step that comes before the final step. Referring to FIG. 5, the predetermined step is set as a step (step 2) that comes before the final step (step 8) and that comes one step before the step (step 3) that can be skipped. Since the step information received by the reception unit 52 indicates the completion of the step 1, the step determination unit 82 determines that the step information does not indicate the predetermined step (step 2).

In this case, the step determination unit 82 instructs the cleaning guide management unit 50 to read the video image file for the next step, and the cleaning guide management unit 50 reads a video image 2 from the cleaning procedure storage unit 54 and supplies the video image 2 to the terminal apparatus 5. Thereby, the terminal apparatus 5 reproduces and displays the video image 2 for the next step on the display.

The video image 2 that is reproduced and displayed on the terminal apparatus 5 is a video image that shows the work details of the step 2 in the endoscope cleaning procedure and shows the way to brush a channel. In this video image, the way to brush each of a forceps channel, a suction channel, an air delivery channel, and a water delivery channel is guided. The cleaning worker looks at the video image 2 displayed on the terminal apparatus 5, checks the correct way of performing the brushing, and brushes each channel. When the brushing of the channels is completed, the cleaning worker enters the completion of the step 2 in the terminal apparatus 5, and the terminal apparatus 5 transmits step information indicating the completion of the step 2 to the management server 10.

At the management server 10, the reception unit 52 receives the step information indicating the completed step. In this case, the reception unit 52 receives the step information indicating that the step 2 has been completed and supplies the step information and the scope ID to the assignment processing unit 80. The reception unit 52 also notifies the recording management unit 94 of the step information, the date and time of the acquisition of the step information, and the scope ID, and the recording management unit 94 records the completion time of the step 2 in the implementation recording unit 96 in connection with the scope ID "105011".

FIG. 6 shows examples of recording details in the implementation recording unit 96. This example shows that the completion time of the step 1 and the completion time of the step 2 are recorded.

The step determination unit 82 determines whether or not the received step information indicates a predetermined step before the final step. In this case, the step information received by the reception unit 52 indicates the step 2, and the step determination unit 82 therefore determines that the received information indicates the predetermined step. Upon receiving this determination result, the cleaning apparatus determination unit 84 determines a cleaning apparatus to be assigned to an endoscope undergoing the manual cleaning based on the relationship between scheduled completion time of the manual cleaning when one or more steps after the predetermined step are skipped and the utilization status of a plurality of cleaning apparatuses 12 managed by the cleaning apparatus management unit 72.

FIG. 7 shows a management table for managing the utilization status of a plurality of cleaning apparatuses 12. The cleaning apparatus management unit 72 according to the embodiment manages the utilization status of the plurality of first cleaning apparatuses 12a to 12d and the plurality of second cleaning apparatuses 12e to 12f. The first cleaning apparatuses 12a to 12d are capable of cleaning endoscopes that have been manually cleaned in a procedure in which the implementation of one or more steps is skipped. The first cleaning apparatuses 12a, 12c, and 12d are of a model XXX, and the first cleaning apparatus 12b is of a model YYYY. The second cleaning apparatuses 12e and 12f cannot clean endoscopes that have been manually cleaned in a procedure in which the implementation of one or more steps is skipped but can only clean endoscopes that have been manually cleaned by performing all the steps.

The cleaning apparatus management unit 72 manages the status and remaining cleaning time in connection with attribute information such as apparatus number and name, a cleaning apparatus model, and a cleaning apparatus ID assigned at the medical facility. The names shown in FIG. 7 are given for convenience in the present specification. In reality, names given at the medical facility may be used. The "status" indicates whether the apparatus is "in use" or "available", and the "remaining cleaning time" indicates the time remaining until the mechanical cleaning is finished. The status and remaining cleaning time shown in a management table in FIG. 7 are as of 10:00:00.

An endoscope that has been manually cleaned is then mechanically cleaned by the cleaning apparatus 12. Before setting the manually cleaned endoscope in a cleaning tank of the cleaning apparatus 12, the cleaning worker causes the ID reader 22 associated with the cleaning apparatus 12 to read the scope ID of the endoscope. When the mechanical cleaning is completed, the cleaning worker removes the endoscope from the cleaning tank and causes the ID reader 22 to read the scope ID of the endoscope. The ID reader 22 transmits the read scope ID to the management server 10 along with the identification information (reader ID) of the ID reader 22 and the identification information (cleaning apparatus ID) of the cleaning apparatus 12 associated with the ID reader 22.

In the management server 10, when the communication unit 30 receives the scope ID, the reader ID, and the cleaning apparatus ID transmitted from the ID reader 22, and the second scope ID acquisition unit 64 acquires the scope ID and the reader ID, and the cleaning apparatus ID acquisition unit 66 acquires the cleaning apparatus ID. The cleaning apparatus management unit 72 receives the scope ID and the cleaning apparatus ID from the second scope ID acquisition unit 64 and the cleaning apparatus ID acquisition unit 66, respectively, as well as acquired time information.

When the cleaning apparatus management unit 72 receives a combination of a scope ID and a cleaning apparatus ID, the cleaning apparatus management unit 72 sets the "status" of the cleaning apparatus ID to "in use". After that, when the cleaning apparatus management unit 72 receives the same combination of the scope ID and the cleaning apparatus ID, the cleaning apparatus management unit 72 sets the "status" to "available". In other words, the cleaning apparatus management unit 72 accepts a combination of a scope ID and a cleaning apparatus ID received first as information indicating the start of the machine cleaning and accepts the same combination of the scope ID and the cleaning apparatus ID received next as information indicating the end of the machine cleaning. The cleaning worker may enter information indicating the start and information indicating the end at the start and end of the mechanical cleaning, respectively.

In a cleaning management system 1 according to the embodiment, the management server 10 can acquire cleaning information from the first cleaning apparatuses 12a to 12d. The first cleaning apparatuses 12a to 12d notify the management server 10 of a selected cleaning program and the remaining cleaning time as cleaning information, and the cleaning information acquisition unit 70 acquires the cleaning information from the first cleaning apparatuses 12a to 12d in the management server 10. This allows the cleaning apparatus management unit 72 to manage the remaining cleaning time for the first cleaning apparatuses 12a to 12d. When a cleaning start button is pressed by a cleaning worker, as cleaning information, the first cleaning apparatuses 12a to 12d may notify the management server 10 of a cleaning completion time set by the selected cleaning program along with information indicating the start of the cleaning.

On the other hand, the second cleaning apparatuses 12e to 12f do not have a function of notifying the management server 10 of cleaning information, and the cleaning apparatus management unit 72 cannot grasp the remaining cleaning time of the second cleaning apparatuses 12e to 12f. Therefore, as shown in FIG. 7, although the cleaning apparatus management unit 72 manages the remaining cleaning time of the first cleaning apparatuses 12a to 12d, the cleaning apparatus management unit 72 does not manage the remaining cleaning time of the second cleaning apparatuses 12e to 12f.

FIG. 8 is a flowchart showing a determination process of a cleaning apparatus. When the step determination unit 82 determines that the step 2 of the manual cleaning has been completed, the cleaning apparatus determination unit 84 derives the scheduled completion time of the manual cleaning when the implementation of the steps 3 to 7 is skipped. Referring to FIG. 3, when the implementation of the steps 3 to 7 is skipped for the manual cleaning of an endoscope of the model AAA, the only remaining step is a step 8, and the cleaning apparatus determination unit 84 knows that the implementation of the step 8 takes approximately three minutes. Therefore, since the completion time of the step 2 is 10:00:00 (see FIG. 6), the cleaning apparatus determination unit 84 derives the scheduled completion time of the manual cleaning when the steps 3 to 7 are skipped as 10:03:00.

The cleaning apparatus determination unit 84 assigns a first cleaning apparatus to the endoscope if the scheduled completion time of the manual cleaning when the implementation of one or more steps is skipped satisfies a predetermined condition for the utilization status of the first cleaning apparatuses 12a to 12d managed by the cleaning apparatus management unit 72. The predetermined condition in this case is that the status is "available" at the scheduled completion time of the manual cleaning. The cleaning apparatus determination unit 84 checks whether there are first cleaning apparatuses that are available at 10:03:00, which is the scheduled completion time of the manual cleaning when the steps 3 to 7 are skipped (S10).

The management table shown in FIG. 7 is as of 10:00:00, and the cleaning apparatus determination unit 84 refers to the status and remaining cleaning time fields so as to determine that the first cleaning apparatuses 12a and 12b are in the "available" status at 10:03:00 (Y in S10). Therefore, the cleaning apparatus determination unit 84 learns that an endoscope with a scope ID "105011" that has been manually cleaned in a procedure in which the steps 3 to 7 are skipped can be cleaned by the first cleaning apparatuses 12a and 12b without delay. As a result, the cleaning apparatus determination unit 84 assigns either one of the first cleaning apparatuses 12a and 12b to the endoscope with the scope ID "105011" (S12). The cleaning apparatus determination unit 84 may assign either one of the first cleaning apparatuses 12a and 12b. In the embodiment, the first cleaning apparatus 12b is assigned to the endoscope.

When the cleaning apparatus determination unit 84 assigns the first cleaning apparatus 12b to the endoscope with the scope ID "105011", the notification unit 90 notifies the cleaning worker of information related to skipping of the implementation of one or more steps. This notification is made to the cleaning worker who is performing the manual cleaning, and the notification unit 90 may display the information related to the skipping of the implementation of one or more steps on the display or may output the information audibly through a speaker of the terminal apparatus 5.

This notification needs to inform the cleaning worker that the next step is a step 8. If the cleaning worker is a skilled worker, since he/she knows that a step 3 is to be performed after the step 2, it is assumed that he/she may start the work in the step 3 immediately after entering the completion of the step 2 into the terminal apparatus 5. Therefore, the notification unit 90 may explicitly display on the display "Please skip steps 3 to 7 and perform step 8" or explicitly give notice of this audibly.

The cleaning apparatus determination unit 84 may instruct the cleaning guide management unit 50 to read a video image file for the step 8, and the cleaning guide management unit 50 may read a video image 8 from the cleaning procedure storage unit 54 and supply the video image 8 to the terminal apparatus 5. Thereby, the terminal apparatus 5 reproduces and displays the video image 8 for the next step on the display. At this time, the cleaning guide management unit 50 functions as a notification unit to inform the cleaning worker that the next step is the step 8.

In the embodiment, since the first cleaning apparatus 12b that mechanically cleans the endoscope is assigned before the completion of the manual cleaning, the notification unit 90 needs to give notice of information identifying the assigned first cleaning apparatus 12b. Thus, the notification unit 90 notifies the cleaning worker of the information identifying the assigned first cleaning apparatus 12b. The notification unit 90 may display on the display of the terminal apparatus 5 the information for identifying the assigned first cleaning apparatus 12*b*, for example, the apparatus number and apparatus name. Alternatively, the notification unit 90 may display information for identifying the endoscope on the display of the terminal apparatus 20*b* corresponding to the assigned first cleaning apparatus 12*b*.

An explanation will be given regarding a flow when there is no first cleaning apparatus that is available at 10:03:00, which is the scheduled completion time of the manual cleaning when the steps 3 to 7 are skipped, in S10 shown in FIG. 8 (N in S10). For convenience of explanation, it is assumed that the first cleaning apparatuses 12*a* and 12*b* do not exist in the following flow. If there is no first cleaning apparatus that is available at 10:03:00 (N in S10), the cleaning apparatus determination unit 84 checks whether the time difference between the cleaning completion time of the first cleaning apparatuses 12*c* to 12*d* and the scheduled completion time of the manual cleaning when the implementation of one or more steps is skipped (10:03:00) is within a predetermined time (S14).

A protein residue is preferably removed from an endoscope as quickly as possible since it becomes more difficult to remove the protein residue as time passes. Therefore, if the time difference is within a predetermined time (e.g., five minutes) (Y in S14), the cleaning apparatus determination unit 84 determines that the steps 3 to 7 of the manual cleaning may be skipped and that a protein residue removal function of the first cleaning apparatus may be used. As a result of the cleaning apparatus determination unit 84 searching the management table for the first cleaning apparatus 12 whose status becomes "available" by 10:08:00, the first cleaning apparatus 12*c* satisfies the condition. Therefore, the cleaning apparatus determination unit 84 assigns the first cleaning apparatus 12*c* as a cleaning apparatus for mechanically cleaning the endoscope with the scope ID "105011" (S16).

On the other hand, if the time difference exceeds the predetermined time (e.g., five minutes) (N in S14), the cleaning apparatus determination unit 84 determines that the steps 3 to 7 of the manual cleaning should not be skipped. Therefore, the cleaning apparatus determination unit 84 instructs the cleaning guide management unit 50 to read a video image file for the step 3, and the cleaning guide management unit 50 reads a video image 3 from the cleaning procedure storage unit 54 and supplies the video image 3 to the terminal apparatus 5. The cleaning apparatus determination unit 84 may derive the scheduled completion time when the manual cleaning is performed by implementing all the steps without skipping steps. If there is any one of the second cleaning apparatuses 12*e* to 12*f* available at that time (Y in S18), the cleaning apparatus determination unit 84 may assign the second cleaning apparatus 12 to the endoscope (S20). If there is no available second cleaning apparatuses 12*e* to 12*f* (N in S18), the cleaning apparatus determination unit 84 may ends this flow without assigning a cleaning apparatus 12 to the endoscope.

In the following, an explanation will be given regarding a process when the steps 3 to 7 are allowed to be skipped and the first cleaning apparatus 12*b* is assigned to the endoscope. The cleaning worker looks at a video image 8 displayed on the terminal apparatus 5 and performs a step of drying the outer surface. When the drying of the outer surface is completed, the cleaning worker enters the completion of the step 8 in the terminal apparatus 5, and the terminal apparatus 5 transmits step information indicating the completion of the step 8 to the management server 10.

At the management server 10, the reception unit 52 receives the step information indicating the completion of the step 8 and notifies the recording management unit 94 of the step information, the date and time of the acquisition of the step information, and the scope ID. The recording management unit 94 records the completion time of the step 8 in the implementation recording unit 96 in connection with the scope ID "105011". At this time, since the completion time of the steps 3 to 7 is not recorded in the implementation recording unit 96, the recording management unit 94 records information indicating that the steps 3 to 7 have not been performed in the implementation recording unit 96.

FIG. 9 shows examples of recording details in the implementation recording unit 96. In this example, the completion times of the steps 1, 2, and 8 are recorded, and information indicating that the steps 3 to 7 have not been performed is recorded.

Upon completing the step 8, the cleaning worker carries the endoscope with the scope ID "105011" to the place of installation of the assigned first cleaning apparatus 12*b* and then causes the ID reader 22*b* to read the scope ID. The ID reader 22*b* transmits the scope ID, the reader ID, and the cleaning apparatus ID to the management server 10. If there is no trouble at this time, the first cleaning apparatus 12*b* is in the "available" status where the apparatus can be used, and the cleaning worker sets the endoscope in the cleaning tank of the first cleaning apparatus 12*b* and starts the mechanical cleaning.

On the other hand, the assigned first cleaning apparatus 12*b* may not be available due to some trouble. At that time, the cleaning worker tries to use an available cleaning apparatus 12. It is assumed that the first cleaning apparatus 12*a* and the second cleaning apparatus 12*e* are available at 10:03:05.

The cleaning worker tries to use the second cleaning apparatus 12*e* and causes the ID reader 22*e* to read the scope ID. In this case, the second cleaning apparatus 12*e* is a cleaning apparatus of a model mmm that does not allow the skipping of the steps 3 to 7, and the endoscope to be mechanically cleaned is an endoscope that has been manually cleaned in a procedure in which the steps 3 to 7 are skipped. The ID reader 22*e* transmits the scope ID, the reader ID, and the cleaning apparatus ID to the management server 10.

In the management server 10, when the communication unit 30 receives the scope ID, the reader ID, and the cleaning apparatus ID transmitted from the ID reader 22*e*, and the second scope ID acquisition unit 64 acquires the scope ID and the reader ID, and the cleaning apparatus ID acquisition unit 66 acquires the cleaning apparatus ID. The usage determination unit 92 determines whether or not implementation information recorded in connection with the scope ID acquired by the second scope ID acquisition unit 64 in the implementation recording unit 96 satisfies the condition for using the second cleaning apparatus 12*e* identified by the cleaning apparatus ID acquired by the cleaning apparatus ID acquisition unit 66. The usage condition for the second cleaning apparatus 12*e* is that the endoscope has been manually cleaned in a procedure in which all the steps have been implemented, and the usage determination unit 92 determines that the condition for using the second cleaning apparatus 12*e* is not met. The usage determination unit 92 then notifies the cleaning worker that the endoscope cannot be mechanically cleaned. This notification may be displayed on the display of the terminal apparatus 20*e* of the second cleaning apparatus 12*e*.

In this case, an endoscope that has been manually cleaned without the steps 3 to 7 can be cleaned by the first cleaning apparatus 12*a*. When the cleaning worker causes the ID reader 22*a* of the first cleaning apparatus 12*a* to read the scope ID, the usage determination unit 92 determines that the implementation information recorded in connection with the scope ID satisfies the condition for using the first cleaning apparatus 12*a*. Thus, the cleaning worker can set the endoscope in the cleaning tank of the first cleaning apparatus 12*a* and perform the mechanical cleaning.

Described above is an explanation on the present disclosure made based on the embodiments. These embodiments are intended to be illustrative only, and it will be obvious to those skilled in the art that various modifications to constituting elements and processes could be developed and that such modifications are also within the scope of the present disclosure.

What is claimed is:

1. An endoscope cleaning management system for managing implementation of a manual cleaning of an endoscope consisting of a plurality of steps, comprising:

one or more processors comprising hardware, wherein the one or more processors are configured to:

receive step information indicating a completed step during the manual cleaning of the endoscope;

determine, based on a user input through a user interface, a scheduled completion time of the manual cleaning of the endoscope when implementation of one or more steps of the plurality of steps is skipped;

determine, based on a status and remaining cleaning time information received from a first cleaning apparatus configured to clean a predetermined type of endoscope that has been manually cleaned in a procedure in which the one or more steps is skipped, an available time at which the first cleaning apparatus becomes available to clean the endoscope; and when the step information received indicates a predetermined step that comes before a final step of the plurality of steps, determine that the available time is after the scheduled completion time of the manual cleaning of the endoscope when implementation of the one or more steps of the plurality of steps is skipped;

in response to determining that the available time is after the scheduled completion time, determine whether a time difference between the available time and the scheduled completion time is within a predetermined time period; and in response to determining that the time difference is within the predetermined time period:

select the first cleaning apparatus to clean the endoscope after the scheduled completion time of the manual cleaning; and control one or more user interfaces to notify a user of the selection of the first cleaning apparatus to clean the endoscope.

2. The endoscope cleaning management system according to claim 1, wherein the one or more processors are configured to:

in response to determining that the time difference is within the predetermined time period, further control the one or more user interfaces to notify the user of the skipping of the implementation of the one or more steps.

3. The endoscope cleaning management system according to claim 1, wherein the one or more processors are configured to:

in response to determining that the time difference is not within the predetermined time period:

determine whether a second cleaning apparatus is configured to clean the predetermined type of endoscope that has been manually cleaned in the procedure in which the one or more steps is skipped; and in response to determining that the second cleaning apparatus is not configured to clean the predetermined type of endoscope that has been manually cleaned in the procedure in which the one or more steps is skipped, control the one or more user interfaces to notify the user that the endoscope cannot be mechanically cleaned.

4. The endoscope cleaning management system according to claim 1, wherein the one or more processors are configured to:

in response to determining that the time difference is not within the predetermined time period:

determine whether a second cleaning apparatus is configured to clean the predetermined type of endoscope that has been manually cleaned in the procedure in which the one or more steps is skipped; and in response to determining that the second cleaning apparatus is configured to clean the predetermined type of endoscope that has been manually cleaned in the procedure in which the one or more steps is skipped:

select the second cleaning apparatus to clean the endoscope after the scheduled completion time of the manual cleaning; and control the one or more user interfaces to notify the user of the selection of the first cleaning apparatus to clean the endoscope.

5. An endoscope cleaning management method for managing implementation of a manual cleaning of an endoscope consisting of a plurality of steps, comprising:

receiving, by one or more processors comprising hardware, step information indicating a completed step during the manual cleaning of the endoscope;

determining, by the one or more processors, based on a user input through a user interface, a scheduled completion time of the manual cleaning of the endoscope when implementation of one or more steps of the plurality of steps is skipped;

determining, by the one or more processors, based on a status and remaining cleaning time information received from a first cleaning apparatus configured to clean a predetermined type of endoscope that has been manually cleaned in a procedure in which the one or more steps is skipped, an available time at which the first cleaning apparatus becomes available to clean the endoscope; and when the step information received indicates a predetermined step that comes before a final step of the plurality of steps, determining, by the one or more processors, that the available time is after the scheduled completion time of the manual cleaning of the endoscope when implementation of the one or more steps of the plurality of steps is skipped;

in response to determining that the available time is after the scheduled completion time, determining, by the one or more processors, a time difference between the available time and the scheduled completion time is within a predetermined time period; and in response to determining that the time difference is within the predetermined time period:

selecting, by the one or more processors, the first cleaning apparatus to clean the endoscope after the scheduled completion time of the manual cleaning; and controlling, by the one or more processors, one or more user interfaces to notify a user of the selection of the first cleaning apparatus to clean the endoscope.

6. The endoscope cleaning management method according to claim 5, further comprising:

in response to determining that the time difference is within the predetermined time period, further controlling, by the one or more processors, the one or more user interfaces to notify the user of the skipping of the implementation of the one or more steps.

7. The endoscope cleaning management method according to claim 5, further comprising:

in response to determining that the time difference is not within the predetermined time period:

determining, by the one or more processors, whether a second cleaning apparatus is configured to clean the predetermined type of endoscope that has been manually cleaned in the procedure in which the one or more steps is skipped; and in response to determining that the second cleaning apparatus is not configured to clean the predetermined type of endoscope that has been manually cleaned in the procedure in which the one or more steps is skipped, controlling, by the one or more processors, the one or more user interfaces to notify the user that the endoscope cannot be mechanically cleaned.

8. The endoscope cleaning management method according to claim 5, further comprising:

in response to determining that the time difference is not within the predetermined time period:

determining, by the one or more processors, whether a second cleaning apparatus is configured to clean the predetermined type of endoscope that has been manually cleaned in the procedure in which the one or more steps is skipped; and in response to determining that the second cleaning apparatus is configured to clean the predetermined type of endoscope that has been manually cleaned in the procedure in which the one or more steps is skipped:

selecting, by the one or more processors, the second cleaning apparatus to clean the endoscope after the scheduled completion time of the manual cleaning; and controlling, by the one or more processors, the one or more user interfaces to notify the user of the selection of the first cleaning apparatus to clean the endoscope.

9. An endoscope cleaning management system that manages implementation of a manual cleaning of an endoscope consisting of a plurality of steps, comprising:

one or more processors comprising hardware, wherein the one or more processors are configured to:

manage utilization status of a first cleaning apparatus that can clean an endoscope that has been manually cleaned in a procedure in which one or more steps are skipped and utilization status of a second cleaning apparatus that cannot clean an endoscope that has been manually cleaned in a procedure in which the one or more steps are skipped but can clean an endoscope that has been manually cleaned by performing all the steps;

acquire first identification information for identifying an endoscope to be manually cleaned;

determine a cleaning apparatus to be assigned to the endoscope based on the utilization status of a plurality of cleaning apparatuses;

receive step information indicating a completed step during the manual cleaning of the endoscope;

record implementation information indicating that the step has been implemented based on the step information received in connection with the first identification information;

acquire the first identification information for identifying an endoscope to be mechanically cleaned;

acquire second identification information for identifying a cleaning apparatus for mechanically cleaning the endoscope;

determine whether or not the implementation information recorded in connection with the first identification information satisfies a condition for using the cleaning apparatus identified by the second identification information; and give notice that the endoscope cannot be mechanically cleaned if the condition for using the cleaning apparatus is not met.

* * * * *